United States Patent [19]

Sun et al.

[11] Patent Number: 5,778,881
[45] Date of Patent: Jul. 14, 1998

[54] METHOD AND APPARATUS FOR DISCRIMINATING P AND R WAVES

[75] Inventors: Weimin Sun, Plymouth; Eric J. Panken, Minneapolis; William J. Combs, Eden Prairie, all of Minn.

[73] Assignee: Medtronic, Inc., Minneapolis, Minn.

[21] Appl. No.: 759,494

[22] Filed: Dec. 4, 1996

[51] Int. Cl.$^6$ .............................................. A61N 5/0402
[52] U.S. Cl. ........................................................ 128/696
[58] Field of Search ................................. 128/696, 920, 128/702

[56] References Cited

U.S. PATENT DOCUMENTS

| | | | |
|---|---|---|---|
| 3,577,983 | 5/1971 | Baessler | 128/702 |
| 3,903,897 | 9/1975 | Woollons et al. | 128/419 |
| 4,365,639 | 12/1982 | Goldreyer | 128/786 |
| 4,721,114 | 1/1988 | DeFault et al. | 128/419 |
| 4,751,931 | 6/1988 | Briller et al. | 128/700 |
| 4,793,361 | 12/1988 | DeFault | 128/696 |
| 4,799,486 | 1/1989 | DeFault | 128/419 |
| 4,825,870 | 5/1989 | Mann et al. | 128/419 |
| 5,000,189 | 3/1991 | Throne et al. | 128/702 |
| 5,092,343 | 3/1992 | Spitzer et al. | 128/733 |
| 5,193,550 | 3/1993 | Duffin | 128/702 |
| 5,280,792 | 1/1994 | Leong et al. | 128/702 |
| 5,292,348 | 3/1994 | Saumarez et al. | 607/5 |
| 5,379,776 | 1/1995 | Murphy et al. | 128/705 |
| 5,400,795 | 3/1995 | Murphy et al. | 128/702 |
| 5,404,880 | 4/1995 | Throne | 128/705 |
| 5,439,483 | 8/1995 | Duoong-Van | 607/5 |
| 5,555,344 | 9/1996 | Zunkler | 395/2.51 |

OTHER PUBLICATIONS

"Use of Hidden Markov Models for Electrocardiographic Signal Analysis," Coast et al., 1990, pp. 184–191.
"An Approach to Cardiac Arrhythimia Analysis Using Hidden Markov Models," Coast et al, Coast at al, 1990, pp. 826–836.
Segmentation of High–Resolution ECGs Using Hidden Markov Models.: Coast, 1993: pp. I–67–I–70.
"Heart Signal Recognition by Hidden markov Models: The ECG Case," Carrault et al., pp. 10–14.

*Primary Examiner*—William E. Kamm
*Attorney, Agent, or Firm*—Thomas F. Woods; Harold R. Patton

[57] ABSTRACT

This is a method and apparatus for the automated discrimination of cardiac events of interest, including P-waves, R-waves, T-waves, and specific arrhythmic sequences, in EGM signals for data storage in an implantable monitor or to control operations of an implantable cardiac stimulator through the use of Hidden Markov Modeling techniques and a reduced set of observations. The number of computations and computation time during a heart cycle is reduced by timing the frames of A-EGM samples to the detection of A-SENSE events by the atrial sense amplifier. The A-EGM sample frame is defined in a window preceding and following each A-SENSE event. The A-EGM sample frames are wavelet transformed, and a number of selected W.T. coefficients for each sample frame are saved in a buffer. Each set of saved W.T. coefficients therefore represents either a P-wave or an intrinsic or paced far field R-wave (including fusion beats) unless noise continuously causes A-SENSE events to occur. When the V-SENSE event occurs, an R-trigger is generated, and each set of saved W.T. coefficients is subjected to the HMM algorithm for a determination as to whether the preceding (and any concurrent) A-SENSE events from which the saved W.T. coefficients were derived are P-waves or R-waves. In addition, when the V-SENSE occurs, the HMM algorithm determines stochastically whether or not the successive sets of saved W.T. coefficients represent P-P sequences, far field R-R sequences or P-R sequences or the like.

18 Claims, 6 Drawing Sheets

R: R-wave
P: P-wave

METHOD AND APPARATUS FOR DISCRIMINATING P AND R WAVES

CROSS-REFERENCE TO RELATED APPLICATION

Reference is hereby made to commonly assigned, co-pending U.S. patent application Ser. No. 08/759,902 filed Dec. 4,1996 entitled "AN ADAPTIVE AND MORPHOLOGICAL SYSTEM FOR DISCRIMINATING P-WAVES AND R-WAVES INSIDE THE HUMAN BODY" naming Weimin Sun et al. as inventors, and having Attorney Docket No. P-3751, the disclosure of which is hereby incorporated by reference herein in its entirety.

FIELD OF THE INVENTION

The present invention relates to facilitation of the automated discrimination of cardiac events of interest, including P-waves, R-waves, T-waves, and specific arrhythmic sequences, in electrocardiograph (ECG) lead signals derived from one or more skin surface electrodes or in one or more electrogram (EGM) derived from one or more electrodes implanted in a patient for data storage in an implantable monitor or to control operations of an implantable cardiac stimulator through the use of Hidden Markov Modeling techniques.

BACKGROUND OF THE INVENTION

In the medical fields of cardiology and electrophysiology, many tools are used to assess the condition and function of a patient's heart from observed frequency, polarity and amplitudes of the PQRST complex associated with a heart cycle. Such tools include the classic external ECG systems for displaying and recording the characteristic 12 lead ECG signals from skin electrodes placed on the patient's chest and limbs, ambulatory ECG Holter monitors for continuously recording the ECG or segments thereof from a more limited set of skin electrodes for a period of time, and more recently developed completely implantable cardiac monitors or cardiac pacemakers and pacemaker/cardioverter/defibrillators (PCDs) or more limited cardioverter/defibrillators (ICDs) having the capability of recording EGM segments or data derived from atrial and ventricular EGMS (A-EGMs and V-EGMs) for telemetry out to an external programmer for external storage and display. The episodes of bradycardia or tachyarrhythmia are typically determined by trained personnel examining the real time or recorded ECGs and EGMs for inadequate, slow heart rates or for excessive or high and irregular heart rates. Through the analysis of patient symptoms and the ECG or EGM, a diagnosis may be made and treatment prescribed, including, in many instances, the implantation of cardiac pacemakers, ICDs or PCDs programmed to detect and respond to the particular episode. As set forth below, the implanted system must be able to appropriately discriminate between the P-wave, R-wave and T-wave in the A-EGM and V-EGM, diagnose any arrhythmic episode and respond appropriately.

Typically, when the EGM or ECG is visually examined, the R-wave is identified as the characteristic marker for a given atrial or ventricular heart cycle, the R-R intervals between successive R-waves are measured to determine a heart rate, and the heart rate is compared against predetermined rate limits to initially classify the heart rate as normal, excessive or inadequate. Inspection for the occurrence, timing and polarity of the associated P-wave and T-wave is made by marking windows from the R-wave and looking for characteristic deviations in the ECG amplitude in those windows. Over a sequence of successive heart cycles, the regularity of the heart rate and the association of P-waves to R-waves are also examined. The existence and nature of arrhythmic episodes can be determined by such exhaustive visual inspection and analysis, assuming that the episode is correctly recorded and optimally if the contemporaneous symptoms can be described by the patient.

In the context of the external ECG, a great deal of effort has been expended over the years to automate the analysis, particularly the analysis of lengthy Holter monitor ECG tapes. Classical approaches taken have included morphology or template matching and feature vector classification to classify QRS complex morphology after R-wave detection and R-R interval determination. Reliable automatic detection of the P-wave using these techniques has not been particularly successful.

More recently, the Hidden Markov Modeling technique has been used in the effort to automate the analysis of ECG recordings to identify the characteristic P-waves and R-waves and to classify heart rhythm. Hidden Markov Modeling is a stochastic technique that has been used very successfully in speech recognition as described by Rabiner, L. R., in "A Tutorial on Hidden Markov Models and Selected Applications" published in *Speech Recognition, IEEE Proceedings* 1989; 77:257–286, incorporated herein by reference in its entirety. Applications of Hidden Markov Modeling techniques to analysis of the external ECGs is described, for example, by Coast, D. A. et al., in: (a) "Use of Hidden Markov Models for Electrocardiogaphic Signal Analysis", *J. Electrocardiol* 1990; 23(suppl): 184–191; (b) "An Approach to Cardiac Arrhythmia Analysis Using Hidden Markov Models", *IEEE Trans Biomed Eng* 1990; 37:826–836; and (c) "Segmentation of High-Resolution ECGS Using Hidden Markov Models", *IEEE*, I-67–70, 1993, all of which are incorporated herein by reference in their entireties. A further article by Thoravel, L. et al., entitled "Heart Signal Recognition by Hidden Markov Models: The ECG Case", in *Meth. Inform Med.*, 1994; 33:10–14, is also incorporated herein by reference in its entirety.

In Hidden Markov Modeling (HMM), the state (or event) sequence of interest is generally not observable, but there is an observable sequence which is statistically related to the interested state sequence from which it is to be inferred. HMM involves two probabilistic functions wherein one represents the occurrence of an interested state (or event) sequence and the other represents the occurrence of an observable sequence related to the state sequence. In the application of HMM techniques to the ECG, it is relatively easy to sample and digitize the ECG values to develop an observation sequence of sample amplitude values. The "hidden" state sequence to be inferred from the sampled observation values is the actual electrical activation sequence of the heart.

The normal heart PQRST electrical activation sequence with intact A-V activation is fairly predictable in shape with the P-wave, R-wave and T-wave events occurring in sequence in the range of normal heart rates and is readily recognized by visual examination of the ECG or transmitted out EGM. Such a sequence is shown in the ECG tracing in FIG. 1. Even this sequence, however, is not as readily identified automatically as described above. In addition, when an A-V dissociation occurs, e.g. A-V block or spontaneous ventricular ectopic events, the PQRST activation sequence is disrupted, and a trained specialist is required to identify the underlying arrhythmia even by sight. In atrial and ventricular tachyarrhythmias, the shapes of the P-waves and R-waves are distorted from the normal sinus rate shapes.

The objective of HMM for event detection and arrhythmia analysis is to detect and differentiate the specific waves and arrhythmic events in terms of state sequences from the observation sequences.

Figure 1:
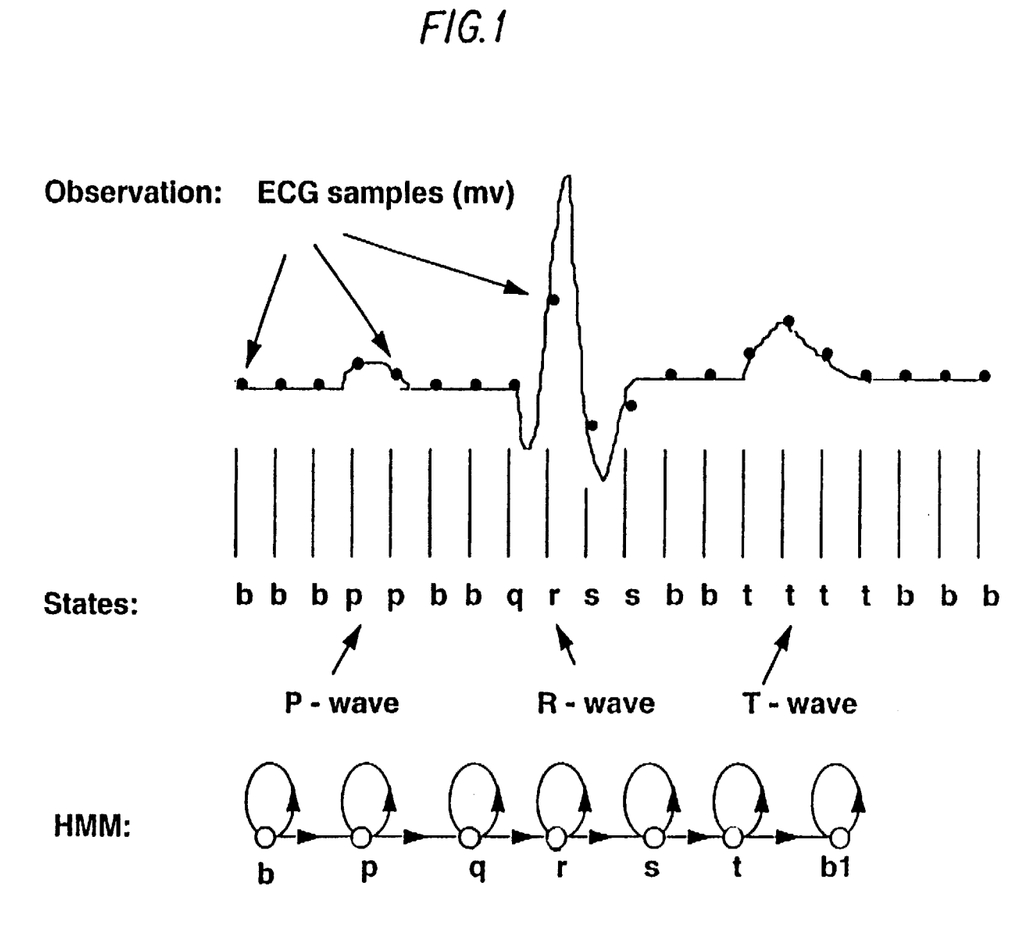
FIG. 1 is a set of tracings illustrating the conventional HMM technique for identifying the PQRST activation sequence from sample values of the ECG.

FIG. 1 is representative of the technique of applying HMM to arryhythmia detection as described in the above-referenced Coast et al. articles. The ECG is sampled at a sample frequency, e.g. 256 Hz. or about every 4 ms, and the sampled values constitute a set of observations that are related to the "states" of a normal left to right HMM depicted in the bottom tracing of FIG. 1 (the number of observations depicted in FIG. 1 are reduced for simplicity of illustration). The observations are characteristic of Baseline (b), Q-wave (q), R-Wave (r), S-wave (s) T-Wave (t), and P-Wave (p) states. These observations are matched against the left to right states of this normal ECG HMM sequence as well as those left to right HMM sequences created to represent differing arrhythmias, e.g. A-V dissociation, ectopic atrial or ventricular beats or the like, to make an assessment as the closest match of the observations in the sequence to the HMM representing a particular rhythm. The differing HMMs are created through a training process from the observation value sets characteristic of each sequence.

In the HMM analysis of cardiac arrhythmias, the sampling rate of the ECG must be fairly high (256 Hz or above) in order to retain morphological information. The HMM analysis is relatively robust and lends itself to discrimination of a number of states of the ECG or EGM representing P-waves, R-waves, T waves and associations thereof characteristic of various tachyarrhythmias as described in the above cited Coast et al. articles. However, the state number and the observation sequence length, for a given time duration of ECG data, is very large. For example, assuming a patient heart rate of 60 beats per minute, the sampling rate is 256 Hz, and two states such as the P-wave and the R-wave state are sought to be determined, the normal HMM has an equivalent state number N=256 and an observation sequence length T=256. In general, the HMM analysis for two states requires a computation proportional to $N^2(T)=1.68\times10^7$. In cardiac arrhythmia analysis by HMM as taught by Coast et al. in article (a) page 191, the actual computation time to complete the HMM analysis using the efficient Viterbi algorithm and a sample rate of 256 Hz took about five times real time or 2.5 hours for a 35 minute ECG tape. Use of hardware accelerators is suggested, but testing apparently has not been reported.

In the above-referenced Thoravel et al. article, other difficulties with the Coast et al. published approaches are raised and solutions explored, particularly devoted to the improvement of the detection of the P-wave from ECG samples employing Modified Continuously Variable Duration HMMs (MCVDHMMs). The ECG sample observations are processed to extract candidate "waves" using a wavelet multiresolution analysis performed on a non-linear transform (NLT) of the ECG samples. The NLT generates transitories with an inflection point corresponding locally to a potential wave peak (observation sample value), and the wavelet transform (W.T.) of the non-linearly transformed observation samples results in magnitude and phase values that can be examined to extract wave features from baseline or "interwave" features. The wave features and sequences can be employed in the MCVDHMM process to identify P-waves, R-waves, etc. and particular rhythms.

While this process may offer advantages over the HMM techniques of Coast et al., still involves a heavy computational burden on the order of that described above for the Coast et al. technique. Consequently, the HMM and MCD-VHMM computation is very expensive, making automatic analysis of ECGs still extremely time consuming and making real time processing of EGM waveforms in an implantable system virtually impossible with current technology.

In this regard, there is a need in implantable, dual chamber, pacemakers, ICDs and PCDs for improved discrimination of P-waves and R-waves in near real time, so that the operations of the implantable pulse generator (IPG) can accurately respond to the underlying current heart rhythm. Typically in such dual chamber IPGs, the amplitude and frequency of the sensed atrial and/or ventricular incoming electrogram signals (A-EGM and V-EGM) are employed in the attempt to distinguish R-waves, P-waves and T-waves from one another and from noise artifacts or other interference. The A-EGM is sensed from a unipolar or bipolar, atrial lead having one or two pace/sense electrodes in contact with the atrium, and the V-EGM is sensed from a unipolar or bipolar ventricular lead having one or two pace/sense electrodes in contact with the ventricle. The atrial and ventricular sense amplifiers employ sense criteria for distinguishing valid P-waves and R-waves, respectively, from far field R-waves and P-waves, respectfully, and electrical noise and artifacts. The filtered A-EGM and V-EGM signal amplitudes are compared against atrial and ventricular sense thresholds, and A-SENSE and V-SENSE events are declared when the A-EGM and V-EGM signal amplitudes exceed the respective thresholds.

The detection of R-waves in the V-EGM is fairly uncomplicated, because the R-wave amplitude usually exceeds the far field P-wave amplitude and most noise signals by a margin allowing the setting of a high ventricular sense threshold. However, because the amplitude of the P-wave is significantly lower than that of the QRS complex and particularly the amplitude of the R-wave in the V-EGM, the atrial sense threshold may be set lower than the ventricular sense threshold. Consequently, the intrinsic R-wave and the ventricular pace (V-PACE) triggered R-wave often appear in the A-EGM conducted by the atrial lead to the atrial sense amplifier and often have an amplitude exceeding the P-wave sense threshold. In this context, the R-wave appearing in the A-EGM signal is referred to as the "far field R-wave", and the sensing of such far field R-waves is referred to as "oversensing".

As described in the above-referenced 759,902 application, many approaches to minimizing oversensing of the far field R-wave from the A-EGM have been attempted, including special electrode designs to minimize the magnitude of the far field R-wave and logic responding to coincidence of V-SENSE and A-SENSE events. At this point in the development of implantable dual chamber pacing systems, the IPG logic and timing circuit sets and times out an atrial sense amplifier blanking period (ABP) and atrial refractory period (ARP) in response to the detection of an A-SENSE event and the triggering of an atrial pace (A-PACE) pulse as well as a further post-ventricular atrial refractory period (PVARP) and blanking period upon a V-SENSE event and delivery of a V-PACE pulse. Similarly, the IPG logic and timing circuit sets and times out a ventricular sense amplifier blanking period (VBP) and refractory period (VRP) in response to the detection of at least a V-SENSE event and the triggering of an A-PACE or V-PACE pulse. The atrial and ventricular sense amplifiers and are effectively disconnected from the atrial and ventricular leads during the ABP and VBP/Respectfully, to protect the respective sense amplifier circuit from high signal levels. Any A-EGM signal passing through the atrial sense amplifier during the longer ARP or PVARP is considered to be noise and not used to reset the V-A escape interval and start the A-V delay interval. Instead, it may be interpreted as a noise artifact and used to actually prolong the refractory period. Similarly, any V-EGM signal passing through the ventricular sense amplifier during the longer VRP is considered to be noise and not used to reset the A-V delay interval and start the V-A escape interval.

P-wave "undersensing" can occur when ventricular depolarizations occur late in the intrinsic heart cycle at the time when an atrial depolarization is about to occur. The atrial and ventricular dissociation results in what is referred to as a "fusion beat". When the R-wave in the V-EGM is sensed, the ABP and PVARP are started, masking both the R-wave signal artifact and the P-wave signal at the input to the atrial sense.

In current IPGs, the blanking periods that are necessary to protect the sense amplifiers and the refractory periods that are used to provide noise detection and protection have minimum lengths that do not vary with pacing rate. Consequently, the use of such blanking and refractory periods can effectively blind the sense amplifiers during a substantial part of the cardiac cycle, particularly as the cardiac cycle shortens at high intrinsic atrial rates. While the cardiac cycle shortens, the delay until the far-field R-wave appears at the atrial electrodes and the width and amplitude of the far-field R-wave as observed at the atrial electrodes remains relatively constant, dictating constant ABP and PVARP intervals. Thus, the ABP and ARP intervals shorten the available time in the heart cycle for sensing legitimate P-waves.

Thus, far field R-wave oversensing is an old problem but gaining greater significance as the new features, e.g., mode switching, atrial arrhythmia monitoring, and tachyarrhythmia detection are implemented in advanced implantable cardiac stimulation devices. These new devices need to sense P-waves at high atrial rates, and low P-wave peak signal amplitudes. Hence, while it is desirable to be able to program a very short atrial refractory period with a high atrial sensitivity to detect such high rate P-waves in the A-EGM, doing so potentially causes oversensing of the signal peaks of far field R-waves. The inability to discriminate far field R-waves from P-waves in the A-EGM may inhibit atrial pacing, degrade A-V synchrony, falsely trigger mode switching, or prevent mode switching during atrial fibrillation.

In PCD systems and related ICD systems for treating atrial arrhythmias, accurate atrial arrhythmia detection is also made difficult by the combination of far field oversensing, undersensing and atrial and/or ventricular blanking and refractory periods. In proposed dual chamber PCD systems having the capability of detecting and treating atrial arrhythmias with at least a limited menu of anti-tachyarrhythmia therapies, also referred to as supraventricular arrhythmias and including atrial fibrillation and atrial flutter, the correct diagnosis of the nature of a detected tachyarrhythmia so that an appropriate treatment can be delivered is crucial. Typically, in proposed dual chamber PCD systems, at least both atrial and ventricular pacing and sensing functions are provided in conjunction with tachyarrhythmia detection and anti-tachyarrhythmia therapy delivery in at least one of the chambers. Such dual chamber PCD systems may only provide atrial anti-tachycardia pacing therapies or may include atrial cardioversion/defibrillation capabilities as further described below. The failure to deliver the appropriate therapy or the delivery of an inappropriate therapy to treat an apparent atrial tachyarrhythmia can progress to or trigger more serious ventricular tachyarrhythmia. Consequently, a great deal of effort has been undertaken to refine the diagnosis of the tachyarrhythmia and to define the appropriate therapy in response to the diagnosis. The accuracy of the diagnosis, particularly of an atrial arrhythmia, is highly dependent on the correct categorization of the sensed event as an R-wave or a P-wave.

The article "Automatic Tachycardia Recognition" by R. Arzbaecher et al., in the journal PACE, May–Jun. 1984, pp. 541–547, discloses an algorithm intended to be implemented in a microprocessor-based implantable system employing both atrial and ventricular rate detection via separate bipolar leads in order to measure the intrinsic or evoked A-A and V-A, or V-V escape intervals and A-V delay intervals in order to distinguish among various types of atrial and ventricular tachycardias, fibrillation or flutter.

Other proposals for employing atrial and ventricular detection and interval comparison are set forth in *The Third Decade Of Cardiac Pacing: Advances in Technology in Clinical Applications*, Part III, Chapter 1, "Necessity of Signal Processing in Tachycardia Detection" by Furman et al. (edited by S. Barold and J. Mugica, Futura Publications, 1982, pages 265–274) and in U.S. Pat. No. 4,860,749 to Lehmann. In both cases, atrial and ventricular rates or intervals are compared to one another in order to distinguish sinus and pathological tachycardias.

In some of these proposed dual chamber PCD systems (and in existing single chamber PCD systems), one or two basic strategies are generally followed. A first strategy is to identify P-waves and R-waves and measure atrial and ventricular intervals and compare them to a preset group of criteria for differing arrhythmias which must be met as precedent to arrhythmia detection or classification. As events progress, the criteria for identifying the various arrhythmias are all monitored simultaneously, with the first set of criteria to be met resulting in detection and diagnosis of the arrhythmia. A second strategy is to define a set of criteria for events, event intervals and event rates which is generally indicative of a group of arrhythmias, and following those criteria being met, analyzing preceding or subsequent events to determine which specific arrhythmia is present. In the Medtronic Model 7219 devices, an arrhythmia detection and classification system generally as disclosed in U.S. Pat. No. 5,342,402, issued to Olson et al., incorporated herein by reference in its entirety, is employed, which uses both strategies together.

To reiterate, in both the dual chamber bradycardia pacing context and the atrial tachyarrhythmia detection context, the accurate detection of R-waves and P-waves is of great importance. The research conducted with HMM detection techniques described above has suggested that the HMM techniques may be valuable in discriminating P-waves from far field R-waves. However, the reported HMM techniques are computationally too demanding and take too much time to be employed in an implantable system where power conservation and size as well as speed are factors of great concern. There is therefore a need for a technique for speeding up HMM analysis of ECGs and providing real time HMM analysis of A-EGM signals while retaining the attributes of HMM detection of individual P-waves, R-waves and T-waves of the PQRST complex and discrimination of arrhythmias.

SUMMARY OF THE INVENTION

It is therefore an object of the present invention to make HMM techniques for detecting P-waves and R-waves more reliable and rapid by reducing computation complexity.

It is a still further object of the present invention to adapt HMM techniques to the automatic detection and discrimination of P-waves from R-waves in real time in implantable medical devices.

It is yet a further object of the present invention to adapt HMM techniques to the discrimination of P-waves from far field R-waves in the A-EGM in near real time in an IPG to facilitate detection of the atrial heart chamber rate to control functions of or the delivery of therapies by the IPG appropriate to the atrial heart rate.

These and other objects of the invention are realized in a wavelet transformation of groups or frames of the sample values of the ECG or EGM to derive a smaller number of W.T. coefficients that are employed as the observations in HMM processing for P-wave detection, R-wave detection, fusion beats, etc. and for arrhythmia analysis in a variety of applications. In our tests, only three to five W.T. coefficients are required to represent up to one hundred sample values of the ECG or EGM in each frame, and, consequently, the length of the W.T. coefficient observation sequence is much smaller than that of the original sample data. Since each frame represents a step in the modeling, the state sequence length is the same as the number of sample frames. Furthermore, since each frame is identified by a state, the total state number used to represent different waves is also much smaller. In other words, the wavelet HMM techniques of the present invention has far fewer observation states and a much shorter state sequence length that contribute to the computation speed-up in the HMM process.

In the context of an implantable pacing system of the types described above having separate atrial and ventricular sensing capabilities and far field R-waves appearing on the A-EGM, the application of the wavelet HMM technique to the near real time detection of P-waves and far field R-waves in the A-EGM may be used for monitoring or diagnostic purposes. The number of computations and computation time during a heart cycle is reduced by timing the frames of A-EGM samples to the detection of A-SENSE events by the atrial sense amplifier. In this case, the A-EGM sample frame is defined in a window preceding and following each A-SENSE event. The A-EGM sample frames are wavelet transformed, and a number of selected W.T. coefficients for each sample frame are saved in a buffer. Each set of saved W.T. coefficients therefore represents either a P-wave or an intrinsic or paced far field R-wave (which may constitute a fusion beat) unless a noise situation occurs that continuously causes A-SENSE events to occur.

When the V-SENSE event occurs, an R-trigger is generated, and each set of saved W.T. coefficients is subjected to the HMM algorithm for a determination as to whether the preceding (and any concurrent) A-SENSE events from which the saved W.T. coefficients were derived are P-waves or R-waves. In addition, when the V-SENSE occurs, the HMM algorithm determines probaballistically whether or not the successive sets of saved W.T. coefficients represent P-P sequences, far field R-R sequences or P-R sequences or the like. In other words, the successive pairs of sets of saved W.T. coefficients are compared with an HMM for a P-R sequence to determine the closest match. The HMM model of the P-R sequence is derived in a training mode, and HMMs of other sequences may also be employed in the process. Diagnostic data may be derived from the HMM model to confirm device operation, and entry into a diagnostic mode may be predicated on a sensed high atrial rate.

In the context of a PCD system or another system for diagnosing and treating atrial tachyarrhythmias, the same process may be followed to ascertain that successive A-SENSE events are actually caused by P-waves and not by oversensing of ventricular events.

Overall detection performance represented by sensitivity and positive predictivity of the two-state wavelet HMM model for either R-wave detection or rejection in atrium is very accurate and reliable. This high accuracy can be anticipated because the HMM model combines both signal morphology information and statistical information in data processing. The role of the wavelet transform used in the HMM analysis is twofold. First the use of wavelet transform significantly reduces the state number and state sequence length for the model, hence improves dramatically the computation efficiency. Second the wavelet transform can retain the basic morphology information of a wave by only a few coefficients. In addition, the use of a probability density function in the HMM for an observation sequence tends to reduces the effect of noise and artifacts.

In a study conducted on a number of patients, only approximately 10 heart cycles of each patient were used for wavelet transform HMM training which is relatively quick and worked very well in the patients. The speed of wavelet HMM training is another advantage of the two-state HMM model and is important for implementation in implantable monitoring and therapeutic systems of the type described above.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

To substantially improve computation efficiency in using HMM techniques for detecting P-waves and R-waves and for arrhythmia detection and classification from the real time ECG or EGM (or for faster analysis of stored ECGs or EGMs), we developed a wavelet HMM technique as described in detail below to vastly reduce the number of computations required over the course of a heart cycle. Particular applications of the wavelet HMM technique for analyzing sets of wavelet transform (W.T.) coefficients associated with event detection follow the following general description of the invention.

As an application of the wavelet HMM for real time R-wave detection in an EGM, we start with the sampled EGM data. Assume first that the sampled sequential EGM data has a sequence length of T and is represented by:

$$O = \{o_1, o_2, o_3, \ldots, o_T\}$$

where $o_i$ is the ith EGM amplitude sample. Instead of using the sampled sequential data directly as an observation vector in the normal HMM technique, we group the sample data as:

$$O = \{\{o_1, o_2, \ldots, o_m\}, \{o_{m+1}, o_{m+2}, \ldots, o_{m+m}\}, \ldots, \{o_{(n-1)m+1}, o_{(n-1)m+2}, \ldots, o_{(n-1)m+m}\}\}$$

where the multiplication of group number n and group size m equals T. Subsequently, a wavelet transform, such as a Daubechies wavelet or a Morlet wavelet transform of the types described by Daubechies, I. in "Orthonormal Bases of Compactly Supported Wavelets", *Comm Pure and Appl. Math* 1988; 41:909–996 and by Morlet D. et al., in "Wavelet Analysis of High-Resolution Signal-Averaged ECGs in Postinfarction Patients", *J Electrocardiol* 1993; 26:311–320, both incorporated herein by reference in their entireties, is applied to each group in the data. As is well known, the wavelet transform has been widely used in image compression and other signal processing fields. The advantage of a wavelet transform is so called multi-resolution representation, that is, fairly detailed information of the original data can be retained by much fewer coefficients in the wavelet transformed domain. The wavelet coefficient sequence is denoted as:

$$O_w = \{o_{w1}, o_{w2}, o_{w3}, \ldots, o_{wn}\}$$

with $$o_{wj} = \{W_{j1}, W_{j2}, W_{j3}, \ldots, W_{jk}\}$$

where $W_{jk}$ the $k^{th}$ wavelet coefficient of the $j^{th}$ group. The new coefficient group size k is chosen to be much smaller than the original sample data group size m. The wavelet coefficients form the transformed observation sequence $o_{w1}, o_{w2}, o_{w3}, \ldots, o_{wn}$. The new observation sequence to be used in wavelet HMM has a length only 1/mth of the original observation sequence length T. Furthermore, since the original samples are grouped into frames, an HMM can be used to represent the state transitions between R-Wave (R), T-Wave (T), and P-Wave (P) states. There is a probability for a state to transit from one to any of the other states in a given patient that can be defined for a variety of cardiac rhythms. These probabilities for each rhythm are unknown a'priori, but can be estimated with an HMM training procedure in the manner taught in the above-referenced Rabiner reference.

The wavelet HMM is more computationally efficient than the conventional HMM processing. Assume a patient has a heart beat rate of 60 beats per minute and the sampling rate is 256 Hz. To detect waves in each beat of ECG data, the conventional HMM has 256 states and an observation sequence length of 256 observations. The computational complexity of HMM is proportional to $N^2 T$, where N is the number of states and T is the observation sequence length.

For conventional HMMs, the computational complexity is $1.68 \times 10^7$ multiplications per second. For the wavelet HMM, we may group the sampling data into groups with size of m=32, define three states for the different waves ($N_W$=3) and select two wavelet coefficients for each group of data ($C_W$=2). An observation sequence length for each beat is now three ($T_W$=3). In general, a discrete wavelet transform has a computational complexity proportional to km, where k is a constant (e.g., k=8 for the 4 tap Daubechies discrete wavelet transform). Thus, the wavelet transform computational complexity is proportional to $kT_W m$. The wavelet HMM also requires a number of computations proportional to $C_W N_W m$. The total number of computations per second for the wavelet HMM is therefore $kT_W m + C_W N_W^2 T_W$, or 822 multiplications per second. When only two waves need to be discriminated ($N_W$=2, $T_W$=2), the number of computations per second required is only 528 per second. Thus, the difference between the normal HMM technique and the wavelet HMM technique of the present invention for analyzing the PQRST waves of a heart cycle is seen to be significant.

In this manner, the simplification in computation may be applied to the above-described prior art HMM processing techniques for analyzing the ECG or EGM data using a reference point to determine the beginning and end of each heart cycle in the sequences of heart cycles in the ECG or EGM subjected to processing. Once the reference point is determined, the sample values may be grouped about it as described above and the transitions between the defined states can be determined for a heart cycle. From the determined transition sequences, a diagnosis of a heart rhythm can be made.

Figure 2:
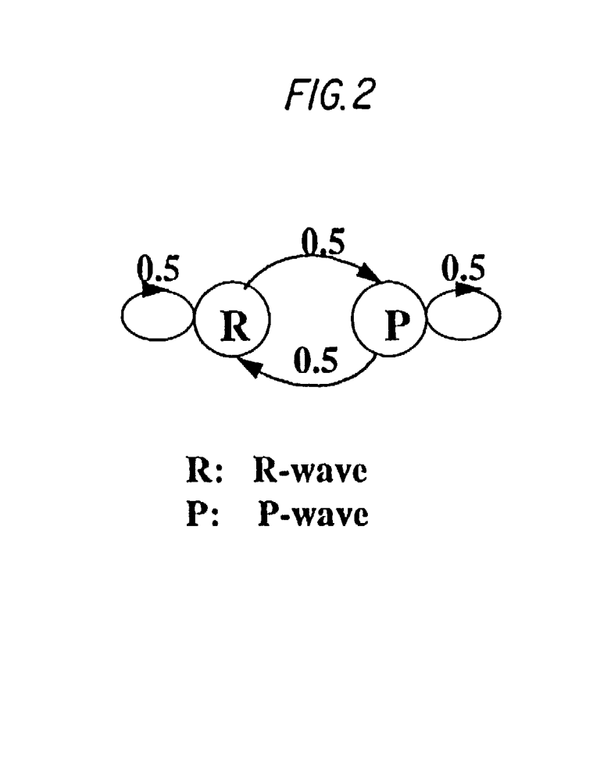
FIG. 2 illustrates a two state HMM of the PQRST complex with stated probabilities for distinguishing P-waves from R-waves.
Figure 3:
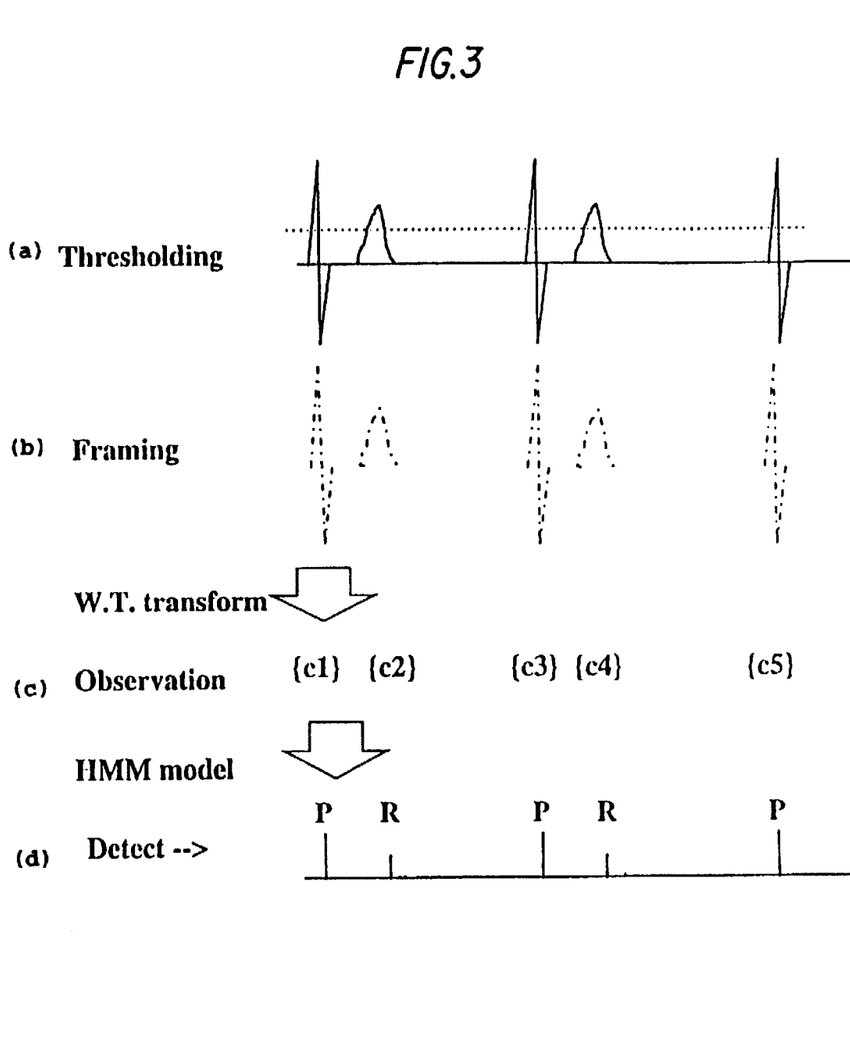
FIG. 3 is a set of tracings illustrating the wavelet HMM technique for identifying the PQRST activation sequence from sample values of the EGM.

FIG. 2 shows a two state model which has been used for far field R-wave detection and rejection in the A-EGM, and FIG. 3 shows waveforms accompanying steps of a preferred embodiment of the present invention wherein a reference point or marker for grouping frames of sample values is defined by a simple thresholding technique. In this simple model, two states, the P-wave (P) and R-wave (R) have been defined. Depending on the atrial rhythm, the probabilities for state transition between the two can be determined in a wavelet HMM training procedure for each patient. As an example, a 0.5 probability has been denoted in FIG. 2 for state transitions between P-waves and R-waves in a patient enjoying normal sinus rhythm. A third state could also be defined for the T-wave, if it is sought to be located, and different state models may be defined for various arrhythmias.

In tracing (a) of FIG. 3, in the first step of this illustration of one preferred embodiment of the present invention, the A-EGM is sampled at a sampling rate of 256 Hz or greater, and each sample value is compared to an atrial sense threshold set low enough to detect all possible waves of interest for the particular patient and determined in a patient work-up. For example, tracing (a) depicts an A-EGM exhibiting a series of P-waves each followed by a far field R-wave both exceeding the atrial sense threshold. When a sample value exceeds the atrial sense threshold, an A-SENSE event is declared, and a group or frame of sample values is defined in step (b). The frame includes m samples in a window on either side of the sample value exceeding the threshold so as to capture most if not all sample values associated with the wave. The samples in each frame are wavelet transformed to obtain a set of representative W.T. coefficients (typically 2 to 4 W.T. coefficients) c1 and c2 as shown in tracing (c). The representative W.T. coefficient set is used as the observations for the wavelet HMM model to determine whether the A-SENSE event is more likely to be a P-wave or an R-wave. The detection result for each P-wave and R-wave is marked differently in tracing (d). The output of the detection identifies the time when the particular wave is detected, and which wave is detected. In a particular implementation of the invention described below, the P-wave and R-wave sequence of tracing (d) in the A-EGM is identified through a P/R wavelet HMM comparison that is initiated on detection of a V-SENSE event.

The representative W.T. coefficients may be selected in a variety of ways. For example, the coefficients with the greatest amplitudes may be selected or coefficients with specified indices may be selected.

Figure 4:
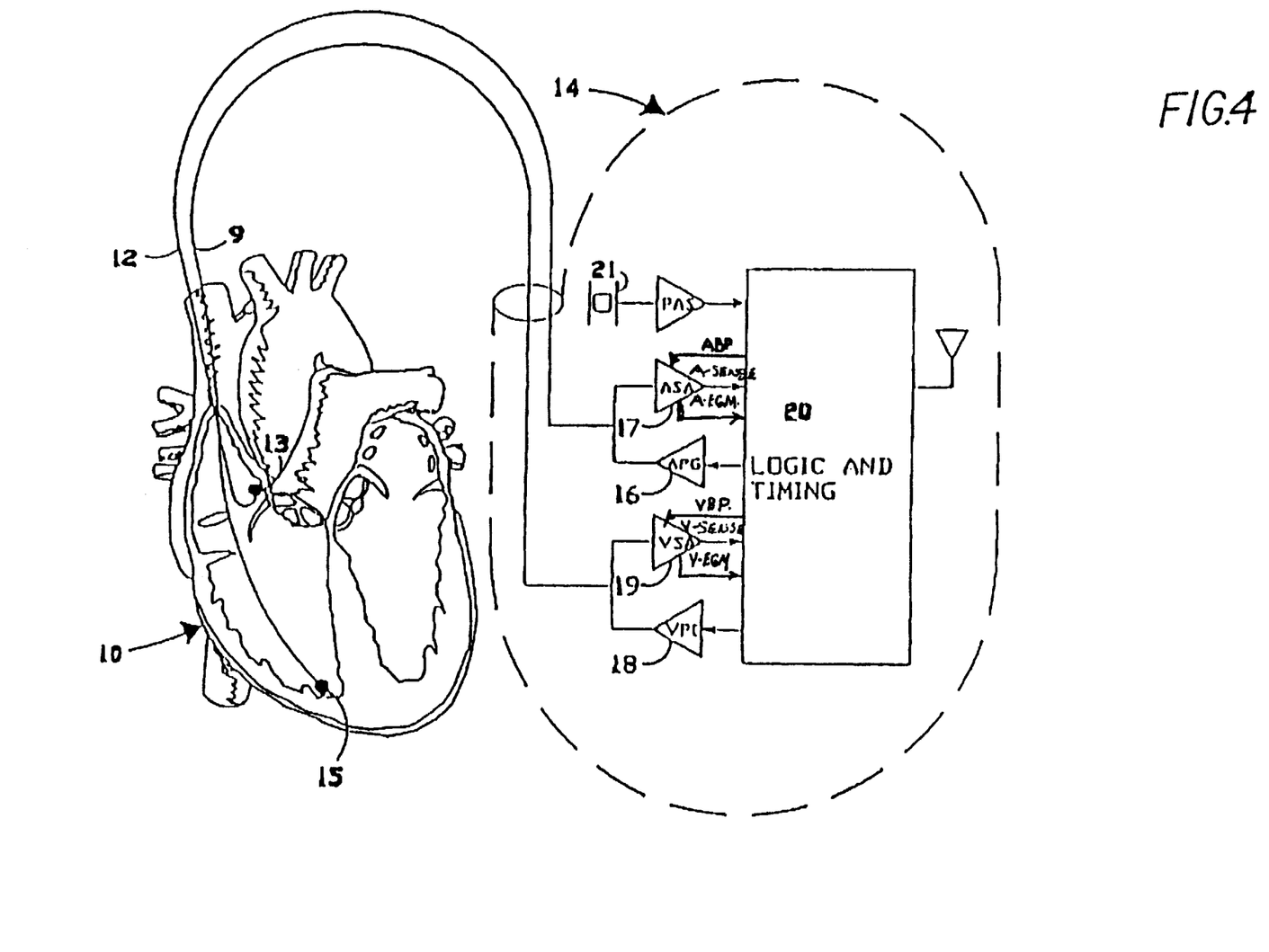
FIG. 4 is a schematic illustration of an implantable dual chamber system for monitoring the A-EGM and V-EGM and, optionally providing stimulation therapies, wherein the wavelet HMM technique of the present invention may be implemented.

FIG. 4 depicts an implantable, dual chamber, cardiac pacing or PCD system (in part) in which the present invention may be incorporated particularly for self diagnosis of oversensing or undersensing of A-SENSE events and in arrhythmia detection. The particular example depicted in FIG. 4 includes atrial and ventricular pacing pulse generators, but it will be understood that these components and pacing operations may be limited to one chamber in the pacemaker or PCD context or omitted entirely in a cardiac monitor context or in an ICD context not including pacing therapies. Thus, FIG. 4 is intended to comprehensively illustrate all such systems and not be limited to the DDD or DDDR pacing context per se.

In FIG. 4 the IPG 14 is coupled with atrial and ventricular leads 12 and 9 extending into the right atrium and ventricle, respectively, of the heart. The IPG 14 is provided with atrial and ventricular sense amplifiers 17 and 19, respectively, coupled through leads 12 and 9, respectively, to atrial electrode(s) 13 implanted in the atrium and ventricular electrode(s) 15 implanted in the ventricles, respectively, that are intended to sense P-waves and R-waves originating in the right atrium and ventricle, respectively. When the IPG 14 is provided with both atrial and ventricular sense amplifiers 17 and 19, it may be programmed or designed with an algorithm for operating in several pacing modes that generally involve using the sensed P-wave to time at least the delivery of a ventricular pacing (V-PACE) pulse by a ventricular pacing pulse generator 18 after an A-V delay unless an R-wave is sensed by the ventricular sense amplifier 19 before time-out of the A-V delay. In the DDDR pacing system depicted in FIG. 1, the IPG 14 is also provided with a logic and timing circuit 20 for setting and timing out the A-V delay and also setting and timing out a V-A escape interval starting on delivery of a ventricular pace pulse or sensing of an R-wave by ventricular sense amplifier 19. The V-A escape interval is itself terminated either by a P-wave sensed by atrial sense amplifier 17 before it times out or delivery of an atrial pacing (A-PACE) pulse by the atrial pacing pulse generator 16 on time-out.

The logic and timing circuit 20 establishes a V-V rate governing the setting of the V-A escape interval that may itself vary depending on a physiologic signal derived from a physiologic sensor, e.g. a patient activity sensor 21, in a manner well known in the art. To the extent that the intrinsic atrial heart rate exceeds the current V-V rate, the recurring P-waves are sensed and control the synchronous pacing rate up to an upper pacing rate limit.

The well known DDD and DDDR pacing mode encompasses atrial and ventricular pacing and sensing and operation in either a synchronous or an inhibited manner depending on the prevailing atrial and ventricular heart rhythm. The related VDD pacing mode provides atrial synchronous, ventricular inhibited pacing, i.e., the DDD pacing mode as described above, but without the atrial pacing capability. In both the DDD and VDD pacing modes, the ability to sense P-waves and distinguish them from R-waves is crucial to avoid inappropriate resetting of V-A escape intervals and/or triggering of synchronous ventricular pacing.

Typically, the input A-EGM is sensed from a unipolar or bipolar, atrial lead 12 having one or two pace/sense electrodes 13 in contact with the atrium and the input V-EGM is sensed from a unipolar or bipolar ventricular lead 9 having one or two pace/sense electrodes 15 in contact with the ventricle. As described above, the typical atrial and ventricular sense amplifiers 17 and 19 employ sense criteria for distinguishing valid P-waves and R-waves, respectively, from electrical noise and artifacts. The input A-EGM and V-EGM signals are filtered to attenuate commonly encountered electrical noise and muscle artifacts and the amplitudes of the signals are compared against A-SENSE and V-SENSE thresholds. When the amplified and filtered A-EGM and V-EGM signal amplitudes exceed the A-SENSE and V-SENSE thresholds, the A-SENSE and V-SENSE event signals are generated. The typical sense amplifiers 17 and 19 in prior art DDD and DDDR pacemakers provide the A-SENSE and V-SENSE event signals to control timing and may also store real time segments of the amplified and filtered A-EGM and V-EGM signal samples, after ADC conversion, for diagnostic purposes.

In accordance with a preferred embodiment of the present invention, the amplified and filtered A-EGM and V-EGM signals are further processed within timing and control circuit 20 as described below in reference to the block diagram of FIG. 5 and flow charts of FIGS. 6 and 7 in a diagnostic operation to determine if successive A-SENSE events in the A-EGM are true P-waves or far field R-waves or represent a fusion beat of a P-wave hidden in a far field R-wave. In this preferred embodiment, the detection of A-SENSE and V-SENSE events is employed in normal sensing operations, and the diagnostic routine may be entered when the sensed atrial rate is excessive, for example. In the latter case, the A-SENSE and V-SENSE events are not employed per se, but could be employed as the P/R trigger and R-trigger signals. The system and process described below may also be implemented in other implantable and external EGM or ECG signal processing systems.

Figure 5:
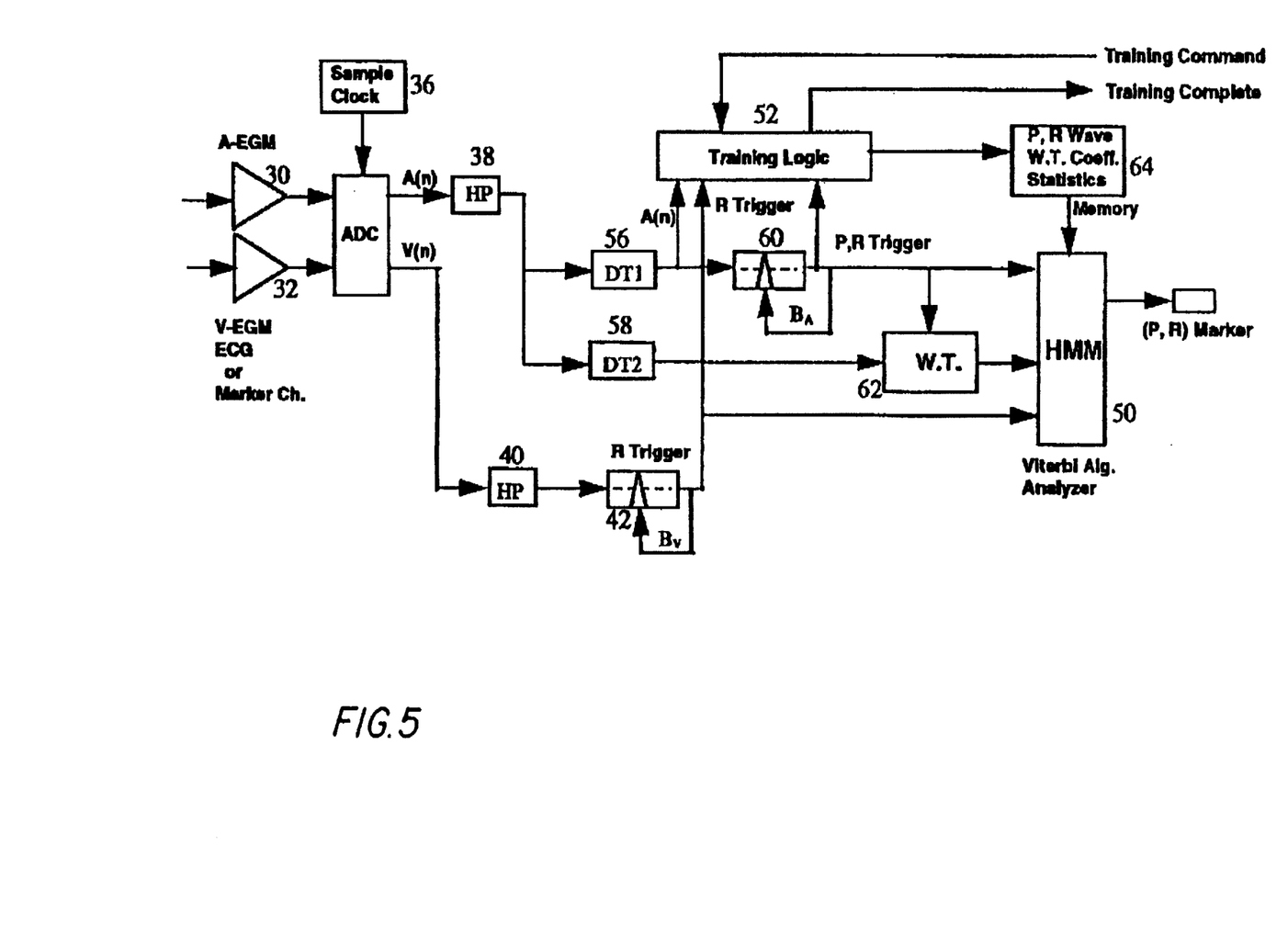
FIG. 5 is a schematic illustration of the architecture of a DSP operating in accordance with the operating algorithm of FIG. 6 and the training algorithm of FIG. 7 that may be incorporated into the present invention.

In FIG. 5 the A-EGM and V-EGM analog input signals are filtered and amplified in amplifier stages 30 and 32, respectively, which may be the initial input stages following the blanking stages of atrial and ventricular sense amplifiers 17 and 19 of FIG. 4. The amplified signals are digitized by ADC 34 at a sampling frequency of at least 256 Hz established by sampling clock 36. The digitized A-EGM samples A(n) and V-EGM samples V(n) are sampled at the same time t(n), and the time stamp of each sample is registered with the sample value and employed in the remaining processing blocks of FIG. 5 and steps of the operating and training algorithms. The digitized A-EGM samples A(n) are digitally filtered in digital filter 38, and the digitized V-EGM samples V(n) are digitally filtered in digital filter 40 to remove any baseline drift in the sample values.

Figure 6:
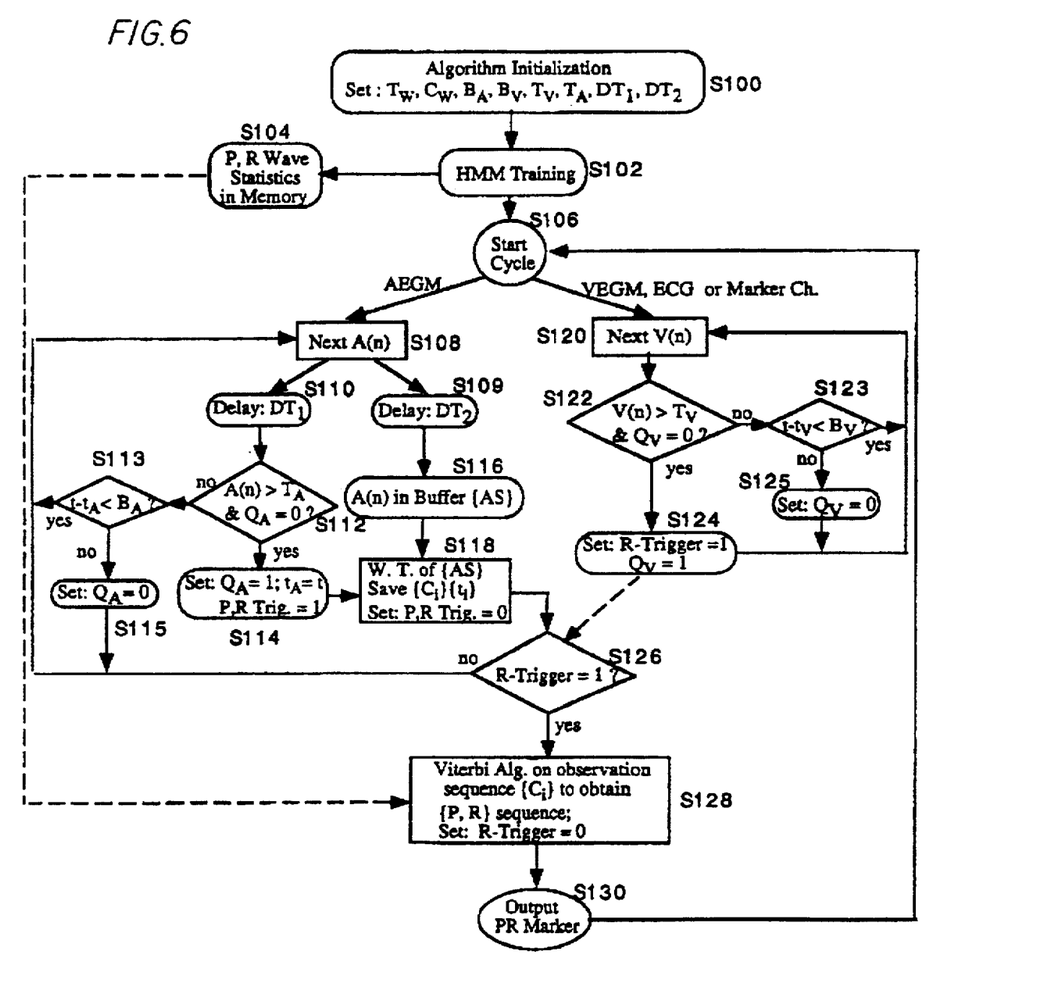
FIG. 6 is a flow chart illustrating the steps of performing the wavelet HMM technique with respect to an ECG or EGM in accordance with the preferred embodiment of the present invention.
Figure 7:
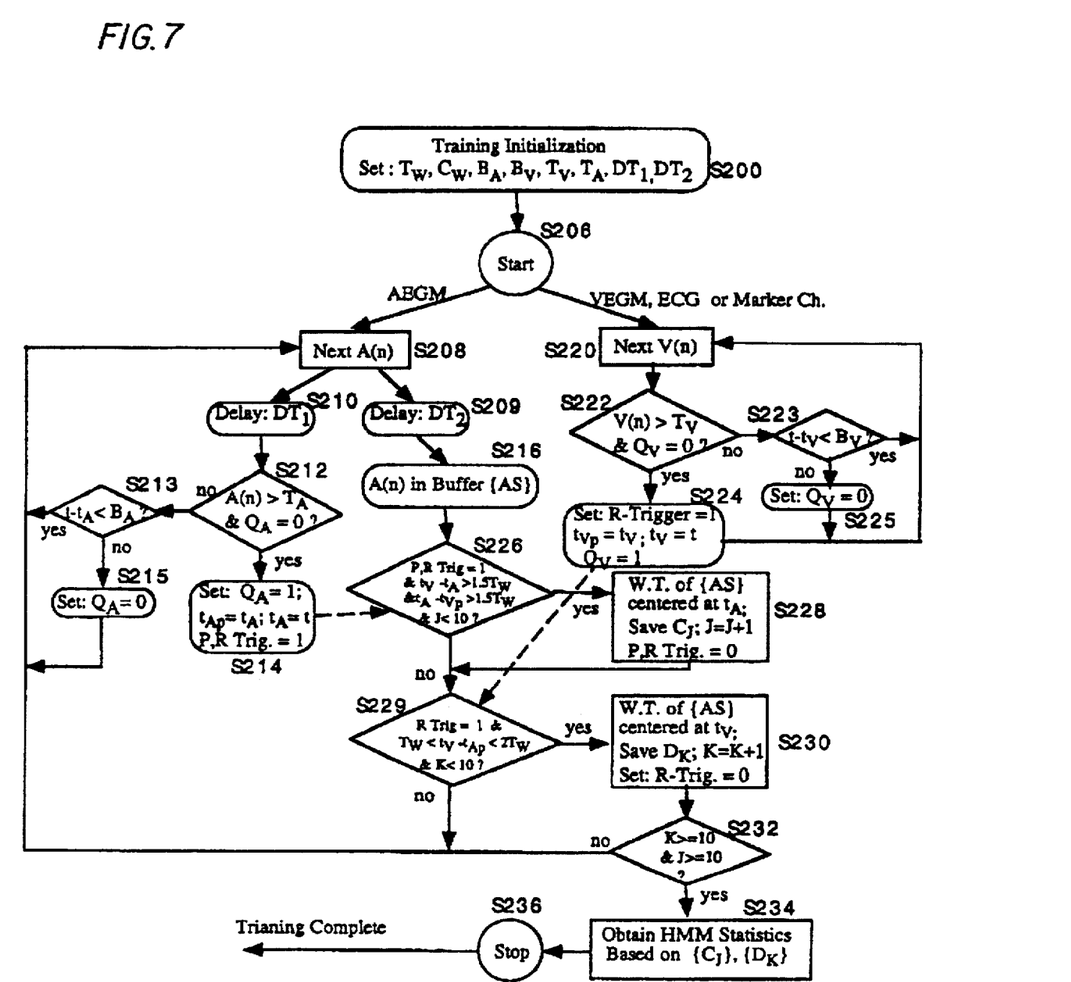
FIG. 7 is a flow chart illustrating the steps of wavelet HMM training usable in the flow chart of FIG. 6 and the architecture of FIG. 5.

In the preferred implementation in DSP, the following operations of the block diagram of FIG. 5 are performed by an algorithm that is programmed in conforming with the operating algorithm flow chart of FIG. 6 and the training algorithm flow chart of FIG. 7. The blocks of FIG. 5 illustrate the architecture and operations of the operating and training algorithms and are simplified to clarify the explanation of this embodiment of the invention.

The filtered ventricular samples V(n) are applied to an R-Trigger threshold comparison block 42, and compared against a programmed R-threshold digital value. When the sample V(n) is greater than the R-threshold value, an R-Trigger is generated within R-Trigger threshold comparator block 42 as long as the state $Q_V$ of a digital blanking timer $B_V$ within R-Trigger threshold comparator is not high ($Q_V=1$). It is assumed that a number of the ventricular samples V(n) will exceed the R-threshold digital value, and it is desired that only a single R-Trigger will be generated when the first ventricular sample V(n) exceeds the R-Trigger threshold.

Assuming that $Q_V=0$, and that an R-Trigger is generated in response to a sample V(n) at the time t(n) associated with it, then $Q_V$ is set to 1, and the time t(n) is registered as the starting time tv of the digital ventricular blanking period $B_V$. The results of the comparison of each subsequent ventricular sample V(n) to the R-Trigger is not allowed to generate a further R-Trigger by operation of the digital blanking timer. The digital blanking timer state $Q_V$ may be reset to 0 by lapse of time or by the count of a number of succeeding ventricular samples in a manner well known in the art. In any case, the initial R-Trigger is a pulse associated with a time t(n) of the ventricular sample V(n) and is applied to the HMM operating block 50 or to the training logic block 52. The HMM block 50 responds by restarting an HMM analysis on the W.T. coefficient sequence buffered during the previous cardiac cycle to determine its state sequence based on the HMM statistics 64 and the Viterbi algorithm in a manner disclosed, for example, in the above-referenced Rabiner reference.

The digitized atrial samples A(n) are applied in parallel paths to DT1 and DT2 delay blocks 56 and 58 that delay the samples A(n) before applying them to a P/R-Trigger threshold block 60 and to a FIFO buffer in W.T. block 62. The delay DT2 is provided to delay the sample A(n) in order to compensate for a relatively lower P/R-threshold employed in the P/R-Trigger block 60 than the R-Trigger threshold employed in the R-Trigger block 42 which somewhat, unintentionally, offsets the delay that it takes for the far field R-wave to reach the atrial sense electrode(s). In other words, DT2 may be needed because the difference in thresholds can result in triggering the generation of the P/R-Trigger in response to an A(n) sample due to a far field R-wave in the A-EGM that is earlier in time than the V(n) sample that triggers an R-Trigger. It is desired to ensure that the R-Trigger occurs earlier than the P/R-Trigger for the same R-wave in order to commence the new processing cycle in the HMM processing block 50.

After the delay DT1, the atrial sample A(n) is applied to the P/R-Trigger block 60, and it operates to generate a P/R-Trigger by comparison of the sample to a programmed P/R-Threshold and as long as the state $Q_A$ of a digital blanking timer $B_A$ within P/R-Trigger block 60 is not high ($Q_V=1$). P/R-Trigger block 60 operates in the same manner as the R-Trigger block 42 described above with respect to the comparison and digital blanking operations. The DT1 delay block 58 is provided in conjunction with the length of an atrial sense (AS) buffer within the W.T. processing block 62 that retains a number preferably twice the number m of A(n) samples on a FIFO basis from which the frame length $T_W$ or number m of samples to be grouped and subjected to the W.T. operation when the P/R-Trigger is generated. In FIG. 4, the P/R-Trigger is generated in block 60 when the digital atrial sense threshold is exceeded (assuming that the digital ventricular blanking period $B_V$ has timed out), and the W.T. operation is then conducted on the frame with m of A(n) samples in the AS buffer. The P/R-Trigger also supplies a time stamp to the triggered W.T. operation.

Referring back to FIG. 3, tracing (c), the framed A(n) samples for the P-waves and far field R-waves are already temporarily stored within the AS buffer when the peak detection of the P-wave and far field R-wave occurs in tracing (a) of FIG. 3 by setting the delay DT1 so that it exceeds the delay DT2 by an amount that ensures that the full frame length $T_W$ of A(n) samples are in the AS buffer when the P/R-TRIGGER is generated. Of course, the triggering of the W.T. operation by P/R-trigger could itself be delayed by a time sufficient to ensure that a full frame of A(n) samples roughly centered on the actual A(n) event exceeding the atrial sense threshold is then stored in the AS buffer.

As described above, the W.T. operation performed in W.T. block 62 on each frame m results in a smaller set of W.T. coefficients $C_W$ that are to be used in the HMM operation in HMM block 50. The coefficients $C_W$ and the P/R-Trigger time stamp are maintained in registers of a coefficient buffer within HMM block 50 until the occurrence of an R-Trigger generated by R-Trigger block 42. The R-Trigger is taken to represent a true R-wave and the end point of the heart cycle and the start of a new heart cycle. On this reference point, the HMM Viterbi algorithm is invoked to make a determination as to the probable sequence represented by the preceding sets of number $C_W$ of coefficients in the coefficient buffer since the last R-Trigger. In that analysis, the sets are used as the observations in the manner described in the above-referenced Coast et al. articles, for example, for HMM processing against stored coefficient sets maintained in training memory 64 that are derived in a training operation based on the patient's own A-EGM characteristics as described below. The models developed in the HMM training include the left to right sequence for normal sinus rhythm depicted in the lower tracing of FIG. 1 as well as left to right sequences for a variety of arrhythmias. Then, based on the probabilistic determination of the sequence that is made in the HMM processing, P-wave and/or R-wave markers are generated that reflect normal sinus rhythm or an arrhythmia.

Turning to FIG. 6, it depicts a flow chart of the operating algorithm paralleling the above described functional description of FIG. 5. Preliminary steps S100, S102 and S104 are conducted at least initially when the implantable or external system is implanted or attached to the patient and then may be repeated periodically by the physician monitoring performance of the system. In step S100, algorithm parameters are initialized and stored in memory to be called up and employed in the appropriate operating architecture blocks of FIG. 4, including the following:

| | |
|---|---|
| N | Number of states defined in each HMM; |
| $T_W$ | Time window or length of W.T. frame of A(n) samples; |
| $C_W$ | The selected W.T. coefficients used to represent each wave in each HMM (assuming more than one HMM); |
| $B_A$ | Atrial channel digital blanking period having state $Q_A$; |
| $B_V$ | Ventricular channel digital blanking period having state $Q_V$; |
| $T_A$ | P/R-Trigger threshold; |
| $T_V$ | R-Trigger threshold; |
| DT1 | AS buffer delay; |
| DT2 | A(n) threshold compensating delay |

In steps S102 and S104, the initial training of the state transition probability matrix is performed pursuant to the training algorithm described below in reference to FIG. 7, and the results are stored in memory to be called up and used in the HMM operations performed in step S128. These include the state transition probability matrices for normal sinus rhythm states and any arrhythmia states as well as the statistics of averaged W.T. coefficient vectors for each defined wave (state).

In step S104, the analysis is started and a number of parallel operations are commenced because of the parallel processing of the A(n) and V(n) samples derived from the A-EGM and V-EGM as depicted in FIG. 5. Starting for convenience with the A(n) sample processing, the next A(n) sample is obtained in step S108 and delayed by DT1 in step S110 and DT2 in step S109. Since DT1>DT2, the delayed A(n) sample is first stored in the AS buffer in step S116. Delay DT1 is related to the sampling frequency and the time window $T_W$ to ensure that m A(n) sample values are stored in the AS buffer before the delayed A(n) sample is compared to the P/R threshold $T_A$ in step S112.

Assuming that the state $Q_A$ of the atrial digital blanking state $Q_A$ is low or 0, then the P/R-Trigger is generated in step S114. At the same time, in step S114, the state $Q_A$ is set high or 1, and the atrial blanking time period start time stamp $t_A$ is set to the time stamp of the triggering A(n) sample. Thereafter, as long as state $Q_A = 1$, the conditions of step S112 cannot be satisfied by subsequent A(n) events. The digital atrial blanking period $B_A$ is timed out in step S113 by subtracting the saved time stamp $t_A$ from the time current stamp t of each subsequent atrial sample A(n) and comparing the result to the digital blanking time $B_A$. When $t-t_A > B_A$, then state $Q_A$ is set to 0 in step S115.

Referring back to step S114, the P/R-Trigger causes a frame of A(n) samples stored in the AS buffer corresponding to the W.T. time window $T_W$ to be wavelet transformed and the resulting number $C_W$ of W.T. coefficients to be temporarily stored in a coefficient buffer in step S118. The P/R-Trigger is also reset in step S118.

At the same time, the next ventricular sample V(n) in step S120 is compared to the ventricular digital threshold $T_V$ in step S122. If the ventricular sample V(n) exceeds the digital threshold $T_V$, and if the ventricular refractory timer state $Q_V$ is at 0, then the R-Trigger and the state $Q_V$ are both set to 1 in step S124. The digital ventricular blanking period $B_V$ is timed out in steps S123 and S125 in the same manner as the atrial blanking period $B_A$ is timed out in steps S113 and S115 described above.

When the R-Trigger is set to 1, the condition of step S126 is satisfied, the HMM Viterbi algorithm is performed on the observation sequence formed of the sets of W.T. coefficients stored in the coefficient register in step S118 using the stored P, R Wave statistics stored in memory in step S104. The R-Trigger is set back to 0 in step S128 and the P-wave and R-wave Markers are outputted in the determined sequence in step S128. When each such Marker is outputted, it is accompanied by a time stamp that subtracts out the delay DT1. The cycle is restarted in step S106.

In the context of the IPG 14 of FIG. 4, the P-wave and/or R-wave markers in the sequence of the immediately concluded heart cycle can be stored in memory for telemetry out in response to a programmed in interrogation command and/or used in a diagnostic routine to confirm that preceding A-SENSE events are truly in response to an intrinsic P-wave and not due to a far field R-wave or noise spikes.

In a dual chamber pacing context, a routine may be entered for determining appropriate ventricular refractory periods or for setting the ventricular sense threshold of the ventricular sense amplifier or for setting an appropriate minimum V-PACE pulse energy level to ensure ventricular capture in manners well known in the art. The same routines may be entered to set atrial sense threshold, atrial refractory period and A-PACE sense thresholds. In the case of a dual chamber pacemaker operating in a rate response mode, the pacing escape interval set in response the physiologic sensor may also be varied to test for an underlying heart rhythm, and differing factors may be tested for establishing the rate response to the sensor output signal. A variety of other diagnostic tests may be undertaken to optimize performance of the pacing or sensing operating algorithms. In each case, the HMM analysis is conducted retrospectively only one heart cycle after the real time occurrences of atrial events, and consequently is in near real time to those events.

In the case of a system for determining whether an arrhythmia exists in either chamber, the HMM analysis can be conducted in the same beat to beat time frame that typical rate, onset and stability arrhythmia determination algorithms rely upon. Consequently, the arrhythmia determinations employing the improved HMM techniques of the present invention may be conducted alone or in parallel with the classic atrial and ventricular arrhythmia determination algorithms.

The training algorithm is invoked in FIG. 5 by a training command received from logic and timing block 20, and a flag indicating completion of the training is provided to logic and timing block 20. Training may be invoked by a programmed in command or when the wavelet HMM algorithm is turned on by a programmed in command. The results of the training are maintained in the memory 64 of FIG. 5. In order to derive the HMM model for each wave of interest and sequence of waves of interest, it is necessary proceed with the training routine. The training routine may be repeated from time to time or upon occurrence of an event, e.g. a change in activity level of the patient, which may be monitored by an activity sensor. For example, when training is initiated, a number, e.g. 10 heart cycles, may be monitored for model training. For each non-fused P-wave identified in the 10 heart cycles, 32 data samples (128 ms) centered at the P-wave peak were stored and wavelet transformed using the four tap Daubechies wavelet transform, for example. After applying the wavelet transform, two wavelet coefficients are selected and used as an observation for the selected P-wave. Each of two coefficients are averaged individually over all P-waves identified for training to obtain a mean and a standard deviation. The mean and standard deviation are used in P-wave observation probability density function in the model. The P-wave observation probability density function is a sum of two univariate Gaussian functions. The identical training procedure is also used for deriving mean and standard deviation coefficients representative of a far field R-wave for each patient.

In experimental verification of this approach, the detection results were saved and verified by visual examination of the atrial electrogram. The true P-wave and far field R-wave locations in the atrial electrogram were manually identified and marked for each patient. These manual markers were used as the control for comparison with the analysis by the HMM model.

In FIG. 7, a training initialization is commenced in step S200 for all of the above listed parameters set in step S100. The parameter values initialized in step S200 are entered by the physician employing an external programmer in a patient work up following a regimen for programming in test values of each parameter, observing results and arriving at optimum values in a manner known in the art. The training algorithm of FIG. 7 then follows the architecture of FIG. 5 and employs many of the same steps as the operating algorithm of FIG. 6. These same steps are numbered in the same order as those appearing in FIG. 6 and described above. Steps S208–S216 and S220–S225 correspond to steps S108–S116 and S120–S125, respectively. The remaining steps differ.

One difference is that time stamps $t_{AP}$ and $t_{VP}$ are maintained for the atrial and ventricular samples A(n) and V(n), respectively, that previously exceeded the digital P/R-Trigger threshold and the R-Trigger threshold and ventricular precede the time stamps $t_A$ and $t_V$, respectively. Separate counters J and K are initially set to 0 and used to count the number of non-overlapping P-waves and far field R-waves to a maximum count 10 in order to obtain meaningful mean and standard deviation values. A buffer $D_K$ is used to store the W.T. coefficients of far field R-waves.

In step S226, when the P/R-Trigger=1 and the counter J count is less than 10, the current P/R-Trigger time stamp $t_A$ is far distant in time from both the previous R-trigger time stamp $t_{VP}$ and the current R-trigger time stamp $t_V$, and therefore can be assumed to result from a true P-wave and not a far field R-wave. In other words, if J<10, $t_V$–$t_A$>1.5 $T_W$, and $t_A$–$t_{VP}$>1.5 $T_W$, these conditions signify that the current signal is a P-wave, because the time stamp $t_A$ is mid-way between two R-wave time stamps $t_V$ and $t_{VP}$. Then, the W.T. operation on the frame m (i.e., $T_W$) A(n) samples in the AS buffer centered at $t_A$ is conducted in step S228. The wavelet coefficient vector $C_j$ is saved and the J counter count is incremented by 1 in step S228. The P/R-Trigger is set to 0 in step S228.

If, the conditions of step S226 are not met at the P/R-Trigger=1 in step S214, or if the operations of step S228 are completed, the conditions at step S229 are examined. When R-Trigger=1 and the counter K count is less than 10, and if the R-trigger is at a reasonable distance in time from the previous P/R-Trigger, it is assumed that there is no P-wave at this time. Then $T_W$<$t_V$–$t_{AP}$<2 $T_W$ which means that the current wave time stamp is distant from the previous atrial wave time stamp $t_{AP}$, but not far distant, and it is most likely a non-overlapping far field R-wave. If all of these conditions are not met, the training is continued to the next atrial sample A(n) is awaited in step S208. If all the conditions are met, then step S230 is commenced.

In step S230, the W.T. operation is commenced on the contents of the AS buffer centered at the time $t_V$ to derive a non-overlapped far field R-wave set of W.T. coefficients. The W.T. coefficients are stored in buffer $D_K$, the counter K count is incremented by 1, and the R-Trigger is set to 0 in step S230. Next, the counts of R-wave capture counter K and P-wave capture counter J are examined in step S232 to determine whether the training should be completed. If both counts are equal to or greater than 10, then the HMM statistics based on the $C_j$ and $D_K$ sets of coefficients. The training algorithm is completed in step S236, and the Training Complete signal is provided to the logic and timing block 20 in FIG. 4 or to an equivalent system in an external embodiment. The training algorithm is automatic once the initial parameters are entered in step S200 and is completed in a short number of cardiac cycles. It may be re-entered from time to time to update the W.T. coefficients.

The present invention may be employed in a variety of cardiac monitoring and therapy providing systems as stated at the outset. In one variation, the signal processing method and apparatus as described above with respect to FIGS. 5 and 6 may be substituted for the atrial and ventricular sense amplifier comparator stages typically incorporated into hybrid circuit sense amplifiers such that the resulting P-Marker and R-Marker signals are used instead of A-SENSE and V-SENSE event signals. In a hybrid combination, the atrial channel A-EGM processing may be conducted using the algorithm of the present invention, but the traditional ventricular channel V-EGM sense amplifier may be used to generate a V-SENSE event signal that is used as the R-Trigger signal applied to the HMM analyzer 50.

The resulting R-Marker and P-Marker signals may be used to trigger or inhibit pacing operations in a dual chamber pacing mode or used in any of the known tachyarrhythmia detection algorithms referred to above to quickly determine whether or not an atrial or a ventricular tachyarrhythmia is present.

The present invention is described above in the context of a multi-programmable, microcomputer based logic and timing circuit 20 with the filtering, timing, comparison, adaptive filtering and morphological functions conducted under the control of algorithms stored in memory. However, the present invention may also be usefully practiced in all such configurations by means of a full custom integrated circuit in each case. For example, such a circuit may take the form of a state machine in which a state counter serves to control an arithmetic logic unit to perform calculations according to a prescribed sequence of counter controlled steps.

In the above-described preferred embodiment, only a two-state HMM was specifically described. In general, a multi-state HMM can be developed for more complicated beats classification or arrhythmia detection. For example, in some patients exhibiting atrial flutter with multiple re-entries or atrial fibrillation. P-waves in the A-EGM could possess different morphologies. In such a case, different P-waves can be defined as different states in an HMM model so that all possible P-waves may be discriminated from one another and from far field R-waves. It should also be noted that when pacing stimulation exists, and/or patients are in exercise, the morphology of P-waves and far field R-waves in the A-EGM will be altered. To discriminate both paced and intrinsic far field R-waves, an HMM model with three or more states may be necessary.

The reliable detection or rejection of far field R-waves in the A-EGM would avoid problems of atrial undersensing or oversensing, thus benefiting patients with more reliable and better atrial arrhythmia detection. In addition, detection of far field R-waves could be a measure for auto-capture in the ventricle and allow discrimination of supra-ventricular tachyarrhythmia from ventricular tachyarrhythmia.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

We claim:

1. A method of identifying P-waves and R-waves in an electrocardiogram using Hidden Markov Modeling (HMM), wherein P-waves and R-waves may each be characterized as a state separated by state transitions in a hidden state sequence and wherein there are discrete probabilities that the states will transition from one to the other in a predetermined order, the method comprising the steps of:

sensing the electrocardiogram from at least one electrode;

continuously sampling the sensed electrocardiogram at a predetermined sampling rate and providing a sample value at each sample time;

detecting an event of interest comprising one of the P-wave or R-wave in the electrocardiogram;

framing a sample data set of sample values as a data frame in response to the detection of an event of interest;

wavelet transforming the data frame of sample values to generate m wavelet transformed coefficients;

selecting a sub-set of wavelet coefficients from among the wavelet coefficients representing an observation vector correlated to each data frame;

applying the HMM algorithm to each observation vector to generate the hidden state sequence; and from the hidden state sequence, determining whether the event of interest is a P-wave or an R-wave.

2. The method of claim 1, wherein the event detection step further comprises:

defining a detection criteria threshold amplitude ensuring that both P-wave and R-wave sample value amplitudes exceed the detection threshold amplitude, and comparing the sample value amplitudes to the detection criteria threshold amplitude and providing an event trigger signifying the occurrence of an event of interest comprising one of the P-wave or R-wave in the intracardiac electrogram when the sample value amplitude exceeds the detection criteria threshold amplitude.

3. The method of claim 2, wherein the framing step further comprises:

retaining a sample data set of at least m sample value amplitudes on a FIFO basis, and in response to detection of an event of interest, framing a sample data set of m sample value amplitudes preceding and following the sample value amplitude satisfying the detection criteria as a data frame.

4. The method of claim 3, further comprising the steps of:

determining the cardiac cycle from a feature of the electrogram;

retaining the observation vectors correlated to each data frame through each cardiac cycle;

applying the HMM algorithm to each observation vector retained through the cardiac cycle to generate the hidden state sequence; and from the hidden state sequence, determining the sequence of P-waves and R-waves in the preceding heart cycle.

5. A method of identifying P-waves and far field R-waves in an atrial electrogram using Hidden Markov Modeling (HMM), wherein P-waves and far-field R-waves may each be characterized as a state separated by state transitions in a hidden state sequence and wherein there are discrete probabilities that the states will transition from one to the other in a predetermined order in a cardiac cycle, the method comprising the steps of:

sensing the atrial electrocardiogram from at least one electrode positioned in sensing relation to the patient's atria;

continuously sampling the sensed atrial electrogram at a predetermined sampling rate and providing an atrial sense sample value at each sample time;

detecting an event of interest comprising one of the P-wave or far field R-wave in the atrial electrogram;

framing a sample data set of m atrial sense sample values as a data frame in response to the detection of an event of interest;

wavelet transforming the data frame of m atrial sense sample values to generate m wavelet transformed coefficients;

selecting $C_W$ wavelet coefficients from among the m wavelet coefficients representing an observation vector correlated to each data frame;

retaining the observation vectors correlated to each data frame through a cardiac cycle;

determining the end of a cardiac cycle correlated to the far field R-wave;

upon determining the end of the cardiac cycle, applying the HMM algorithm to each observation vector retained until the end of the cardiac cycle to generate the hidden state sequence; and from the hidden state sequence, determining whether the event of interest is a P-wave or an R-wave.

6. The method of claim 5, wherein the event detection step further comprises:

defining a P/R-Trigger threshold amplitude ensuring that both P-wave and R-wave representative atrial sense sample value amplitudes exceed the P/R-Trigger threshold amplitude;

comparing the atrial sense sample value amplitudes to the P/R-Trigger threshold amplitude; and providing a P/R-Trigger signifying the occurrence of an event of interest comprising one of the P-wave or far field R-wave in the atrial electrogram when the atrial sense sample value amplitude exceeds the P/R-Trigger threshold amplitude.

7. The method of claim 6, wherein the framing step further comprises:

retaining a sample data set of at least m atrial sense sample value amplitudes on a FIFO basis; and in response to a P/R-Trigger, framing a sample data set of m sample value amplitudes preceding and following the atrial sense sample value amplitude satisfying the P/R-Trigger threshold amplitude as a data frame.

8. The method of claim 7, wherein the step of determining the end of the cardiac cycle further comprises:

sensing the ventricular electrogram from at least one electrode positioned in sensing relation to the patient's ventricles;

detecting the R-wave from the sensed ventricular electrogram; and providing an R-trigger from the detected R-wave signifying the end of the cardiac cycle.

9. The method of claim 7, wherein the step of determining the end of the cardiac cycle further comprises:

sensing the ventricular electrogram from at least one electrode positioned in sensing relation to the patient's ventricles;

continuously sampling the sensed ventricle electrogram at a predetermined sampling rate and providing a ventricular sense sample amplitude at each sample time;

defining an R-Trigger threshold amplitude ensuring that the R-wave peak sample amplitude exceeds the R-Trigger threshold amplitude; and comparing the amplitude of each ventricular sense sample amplitude to the R-Trigger threshold amplitude and providing an R-Trigger signifying the end of the cardiac cycle when the ventricular sense sample amplitude exceeds the R-Trigger threshold amplitude.

10. An apparatus for identifying P-waves and R-waves in an electrocardiogram using Hidden Markov Modeling (HMM), wherein P-waves and R-waves may each be characterized as a state separated by state transitions in a hidden state sequence and wherein there are discrete probabilities that the states will transition from one to the other in a predetermined order, the apparatus further comprising:

means for sensing the electrocardiogram from at least one electrode;

means for continuously sampling the sensed electrocardiogram at a predetermined sampling rate and providing a sample value at each sample time;

means for detecting an event of interest comprising one of the P-wave or R-wave in the electrocardiogram;

means for means for framing a sample data set of sample values as a data frame in response to the detection of an event of interest;

means for wavelet transforming the data frame of sample values to generate m wavelet transformed coefficients;

means for selecting a sub-set of wavelet coefficients from among the wavelet coefficients representing an observation vector correlated to each data frame;

means for applying the HMM algorithm to each observation vector to generate the hidden state sequence; and from the hidden state sequence, determining whether the event of interest is a P-wave or an R-wave.

11. The apparatus of claim 10, wherein the event detection means further comprises:

means for defining a detection criteria threshold amplitude ensuring that both P-wave and R-wave sample value amplitudes exceed the detection threshold amplitude; and means for comparing the sample value amplitudes to the detection criteria threshold amplitude and providing an event trigger signifying the occurrence of an event of interest comprising one of the P-wave or R-wave in the intracardiac electrogram when the sample value amplitude exceeds the detection criteria threshold amplitude.

12. The apparatus of claim 11, wherein the framing means further comprises:

means for retaining a sample data set of at least m sample value amplitudes on a FIFO basis; and means responsive to detection of an event of interest for framing a sample data set of m sample value amplitudes preceding and following the sample value amplitude satisfying the detection criteria as a data frame.

13. The apparatus of claim 12, further comprising:

means for determining the cardiac cycle from a feature of the electrogram;

means for retaining the observation vectors correlated to each data frame through each cardiac cycle;

means for applying the HMM algorithm to each observation vector retained through the cardiac cycle to generate the hidden state sequence; and means for determining the sequence of P-waves and R-waves in the preceding heart cycle from the hidden state sequence.

14. An apparatus for identifying P-waves and far field R-waves in an atrial electrogram using Hidden Markov Modeling (HMM), wherein P-waves and R-waves may each be characterized as a state separated by state transitions in a hidden state sequence and wherein there are discrete probabilities that the states will transition from one to the other in a predetermined order in a cardiac cycle, the apparatus comprising:

means for sensing the atrial electrocardiogram from at least one electrode positioned in sensing relation to the patient's atria;

means for continuously sampling the sensed atrial electrogram at a predetermined sampling rate and providing an atrial sense sample value at each sample time;

means for detecting an event of interest comprising one of the P-wave or far field R-wave in the atrial electrogram;

means for framing a sample data set of m atrial sense sample values as a data frame in response to the detection of an event of interest;

means for wavelet transforming the data frame of m atrial sense sample values to generate m wavelet transformed coefficients;

means for selecting $C_w$ wavelet coefficients from among the m wavelet coefficients representing an observation vector correlated to each data frame;

means for retaining the observation vectors correlated to each data frame through a cardiac cycle;

means for determining the end of a cardiac cycle correlated to the far field R-wave;

means operable upon determining the end of the cardiac cycle for applying the HMM algorithm to each observation vector retained until the end of the cardiac cycle to generate the hidden state sequence; and means for determining from the hidden state sequence whether the event of interest is a P-wave or an R-wave.

15. The apparatus of claim 14, wherein the event detection means further comprises:

means for defining a P/R-Trigger threshold amplitude ensuring that both P-wave and R-wave representative atrial sense sample value amplitudes exceed the P/R-Trigger threshold amplitude;

means for comparing the atrial sense sample value amplitudes to the P/R-Trigger threshold amplitude; and means for providing a P/R-Trigger signifying the occurrence of an event of interest comprising one of the P-wave or far field R-wave in the atrial electrogram when the atrial sense sample value amplitude exceeds the P/R-Trigger threshold amplitude.

16. The apparatus of claim 15, wherein the framing means further comprises:

means for retaining a sample data set of at least m atrial sense sample value amplitudes on a FIFO basis; and means responsive to a P/R-Trigger for framing a sample data set of m sample value amplitudes preceding and following the atrial sense sample value amplitude satisfying the P/R-Trigger threshold amplitude as a data frame.

17. The apparatus of claim 16, wherein the means for determining the end of the cardiac cycle further comprises:

means for sensing the ventricular electrogram from at least one electrode positioned in sensing relation to the patient's ventricles;

means for detecting the R-wave from the sensed ventricular electrogram; and means for providing an R-trigger from the detected R-wave signifying the end of the cardiac cycle.

18. The apparatus of claim 16, wherein the means for determining the end of the cardiac cycle further comprises:

means for sensing the ventricular electrogram from at least one electrode positioned in sensing relation to the patient's ventricles;

means for continuously sampling the sensed ventricle electrogram at a predetermined sampling rate and providing a ventricular sense sample amplitude at each sample time;

means for defining an R-Trigger threshold amplitude ensuring that the R-wave peak sample amplitude exceeds the R-Trigger threshold amplitude; and means for comparing the amplitude of each ventricular sense sample amplitude to the R-Trigger threshold amplitude and providing an R-Trigger signifying the end of the cardiac cycle when the ventricular sense sample amplitude exceeds the R-Trigger threshold amplitude.

* * * * *